United States Patent [19]

Sunderland

[11] Patent Number: 5,170,817
[45] Date of Patent: Dec. 15, 1992

[54] SUPPORT DEVICE FOR FLUID DELIVERY SYSTEM AND CASE THEREFORE

[75] Inventor: Richard A. Sunderland, St. Charles, Mo.

[73] Assignee: Sherwood Medical Company, St. Louis, Mo.

[21] Appl. No.: 679,886

[22] Filed: Apr. 3, 1991

[51] Int. Cl.⁵ .............................................. F16L 3/00
[52] U.S. Cl. .............................. 137/343; 137/355.28; 128/DIG. 12; 604/151; 417/360
[58] Field of Search .................. 417/360; 604/151; 248/346; 137/343, 565, 355.16, 355.28; 128/DIG. 12

[56] References Cited

U.S. PATENT DOCUMENTS

| | | | |
|---|---|---|---|
| 3,228,474 | 1/1966 | Huthsing, Jr. | 169/31 |
| 3,880,188 | 4/1975 | Oakley, Jr. et al. | 137/355.28 |
| 3,972,649 | 8/1976 | Jutte | 417/53 |
| 4,207,889 | 6/1990 | Oloff et al. | 604/152 |
| 4,311,050 | 1/1982 | Bessman | 73/427 |
| 4,397,639 | 8/1983 | Fschweiler et al. | 128/DIG. 12 |
| 4,416,595 | 11/1983 | Cromie | 417/476 |
| 4,479,761 | 10/1984 | Bilstad et al. | 417/395 |
| 4,507,112 | 3/1985 | Hillel et al. | 604/65 |
| 4,513,796 | 4/1985 | Miller et al. | 141/83 |
| 4,545,783 | 10/1985 | Vaughan | 604/259 |
| 4,657,486 | 4/1987 | Stempfle et al. | 417/12 |
| 4,688,595 | 8/1987 | Srebnik et al. | 137/343 |
| 4,699,613 | 10/1987 | Donawick et al. | 604/80 |
| 4,720,636 | 1/1988 | Benner, Jr. | 250/573 |
| 4,722,734 | 2/1988 | Kolin | 128/DIG. 12 |
| 4,832,584 | 5/1989 | Nassif | 417/477 |
| 5,011,378 | 4/1991 | Brown et al. | 417/360 |
| 5,057,081 | 10/1991 | Sunderland | 604/153 |

FOREIGN PATENT DOCUMENTS

8601413  3/1986  World Int. Prop. O. .......... 604/151

OTHER PUBLICATIONS

Ross Laboratories, *Introducing Flexiflo Companion Enteral Nutrition Pump*, Feb. 1988, 2 pages.
Ross Laboratories, *Flexiflo Companion Enteral Nutrition Pump Operating Manual*, Aug. 1987, pp. 1–16.
Fresenius AG, *Frenta-System for Continuous Tube Feeding, Instruction For Use,* 1983, 13 pages.

*Primary Examiner*—A. Michael Chambers
*Attorney, Agent, or Firm*—Andrew J. Beck; Montgomery W. Smith; Gene B. Kartchner

[57] ABSTRACT

The present invention relates to a support device for use with a fluid delivery system which includes a fluid delivery set and an infusion pump. The support device allows simple attachment of various types of fluid delivery sets and infusion pumps thereto and is adapted for use with bed ridden patients in a traditional manner, or for ambulatory patient use. The support device includes a compartment for securely holding an infusion pump and a separate compartment for securely holding a fluid container of the fluid delivery set. The device further includes an elongate channel into which the tubing of the fluid delivery set can be inserted and subsequently protected from kinking or inadvertent occlusion. The support device is adapted for use with rigid bottle, flexible bag, burette, spike sets, or other standard types of fluid delivery sets, and may be used on an infusion pole in a standard manner, located on a horizontal surface such as a table, or enclosed in a carrying case for ambulatory use. Also disclosed are uniquely designed carrying cases for receiving the support device.

27 Claims, 12 Drawing Sheets

SUPPORT DEVICE FOR FLUID DELIVERY SYSTEM AND CASE THEREFORE

BACKGROUND OF THE INVENTION

1. Field of the Invention

This invention relates generally to a fluid delivery system. More specifically, the present invention relates to a support device used as a part of a fluid delivery system for supporting and protecting elements thereof, e.g. pump, fluid container, tubing, drip chamber, etc. of a fluid infusion system.

2. Description of the Prior Art

It is common for patient's having certain medical problems to require periodic premeasured infusions of fluid, such as medicaments or nutrients, into their bodies. Examples of such patients are those who may require nutrients to be delivered directly into their digestive tract periodically over long periods of time, or cancer patients who require exacting amounts of medication to be delivered intravenously at precise periods of time.

In the past, such patients required hospitalization for the time necessary to infuse the nutrient or medicaments in order to allow medical personnel to perform the infusions at the proper time and in the proper amounts. Such a procedure was extremely time consuming to the patient and also the hospital personnel, and had the potential of human error in calculation of infusion dosages and injection time intervals.

An improvement on the above procedure has been to employ a programmable pump to insure that the patient receives the proper infusion dosage at the proper time period, thus relieving medical personnel from constant monitoring of the patient, and from worrying about infusion amounts and time tables. Although the programmable pump greatly relieves medical personnel of time consuming care to the patient, the patient nevertheless remains bound to the hospital bed during the prolonged infusion periods.

A further improvement has been to develop an infusion system which can not only automatically infuse preset volumes of fluid into the patient on a predetermined time table, but also allow the patient to be ambulatory. U.S. Pat. No. 4,657,486 to Stemple et al. is exemplary of portable infusion systems of this type. Stemple discloses a portable infusion device which is automatically operable at selected time intervals to inject accurate amounts of fluid medication into a patient's body, and is also sufficiently compact and portable to allow the patient to be ambulatory while being attached to the infusion system.

U.S. Pat. No. 4,688,595 to Srebnik et al. is also exemplary of fluid delivery systems of this type. Srebnik discloses a delivery system which includes an integrally molded base to which elements of the delivery system, i.e., the pump, the fluid container, etc. can be connected. The base allows the entire fluid delivery system to be transportable as a unit and makes it possible for the patient to move about without the inconvenience of transporting a more cumbersome apparatus such as a prior art type infusion system affixed to a pole mounted on wheels.

Although there has been improvement in portable fluid delivery systems in the past, there nevertheless remain several inadequacies. First, fluid infusion systems generally include a programmable pump and a fluid delivery set comprising a fluid container, tubing, a pinch clamp, a drip chamber, etc. all connected as an integral unit. The container of the fluid delivery sets may be a flexible bag, a rigid glass or plastic bottle or a burette. Sometimes standard fluid delivery sets (i.e. sets intended for non-ambulatory use) include rather long tubular extensions to allow the fluid container to be placed on an infusion pole while the distal end of the tube can be attached to a bed ridden or non-ambulatory patient. These sets are generally ill suited for placement in a portable device such as that described by Srebnik et al. This is because the portable system requires significantly shorter tubing extension to properly operate. The excess tubing therefore becomes cumbersome and inhibitive of proper operation of the system and often becomes occluded or pinched off during ambulatory use. Alternatively, systems such as that shown by Stemple et al. require a unique "non-standard" tubing design in order to allow the fluid delivery set to be properly attached to the pump. This has been found to be unsatisfactory in that it requires the hospital or other facility to stock the "non-standard" fluid delivery sets for use in the ambulatory type systems and standard sets for all other uses, since the "non-standard" ambulatory sets shown by Stemple et al. are generally unsuitable for use on standard non-ambulatory systems.

OBJECTS AND SUMMARY OF THE INVENTION

Briefly, and in general terms, the present invention provides for ambulatory use of a "standard" pump and fluid delivery set of a fluid delivery system while reliably preventing kinking or occlusion of excess tubing thereof and other inadvertent damage to the system.

It is an object of the present invention to provide a portable fluid delivery system which is designed to accommodate standard fluid delivery sets therewith.

It is another object of the present invention to provide a fluid delivery system which is designed to avoid occlusions or damage to the tubing of fluid delivery sets.

It is another object of the present invention to provide a support device for a fluid delivery system which will allow use of standard fluid delivery sets (designed for non-ambulatory use) thereon and which will protect and avoid occlusion of the excess tubing thereof.

It is another object of the present invention to provide a support device which is readily adaptable for use with soft bag, blow molded bottle, glass bottle, or burette-type fluid containers of fluid delivery sets.

It is a further object of the present invention to provide a support device which allows for the pump of a fluid delivery system to be readily attached or detached therefrom.

It is another object of the present invention to provide a support device which can be used either free-standing, attached to an infusion pole, or enclosed in a carrying case.

These and other objects of the present invention are realized in a specific preferred embodiment thereof, disclosed for purposes of example and not by way of limitation, which comprises a support device formed of a rigid body having a receptacle for receiving and locking a standard infusion pump in place therein, and a generically-shaped area for receiving and retaining a container of a fluid delivery set in a fixed position relative to the pump. The support device also includes an elongated channel extending around a substantial portion of the perimeter of the rigid body into which the tubing of the fluid delivery set can be inserted. The elongate channel is designed to match the length of the tubing included on a "standard" fluid delivery set so that tubing between the container and the pump is protected against kinking or occlusion along its entire length. The rigid body also includes straps, brackets, and clamps which are strategically positioned to provide maximum support for anyone of several types of containers, such as soft bags, glass bottles, blow molded plastic bottles, burettes, etc. The rigid body also includes a base which can be used to support the entire fluid delivery system, and which may include extendable legs to increase the stability thereof. Alternatively, the rigid body may include a hole which allows it to be suspended from a standard infusion pole. Further, a carrying case designed to allow ready access to operation of the pump or visualization of fluid levels in the container can be placed about the support device. The case may include a strap or other type of handle to allow the patient to transport the entire fluid delivery system without concern for kinking or occlusion of the fluid set tubing, or for other damage to the system.

These and other objects and advantages of the present invention will become apparent from the following more detailed description, when taken in conjunction with the accompanying drawings in which like elements are identified with like numerals throughout.

BRIEF DESCRIPTION OF THE DRAWINGS

FIG. 4 is a cross-sectional view of the tube channel of the support device taken along line IV—IV of FIG. 3;

FIGS. 5(a-d) are perspective views of a preferred embodiment of the support device of the present invention showing a pump and fluid set of a fluid delivery system in various stages of attachment and assembly to the support device;

DETAILED DESCRIPTION OF THE PREFERRED EMBODIMENTS

As shown in the exemplary drawings for the purposes of illustration, an embodiment of a support device made in accordance with the principles of the present invention, referred to generally by the reference numeral 10, is provided for convenient support of a standard (non-ambulatory type) fluid set and an infusion pump of a fluid delivery system for ambulatory use.

Figure 1:
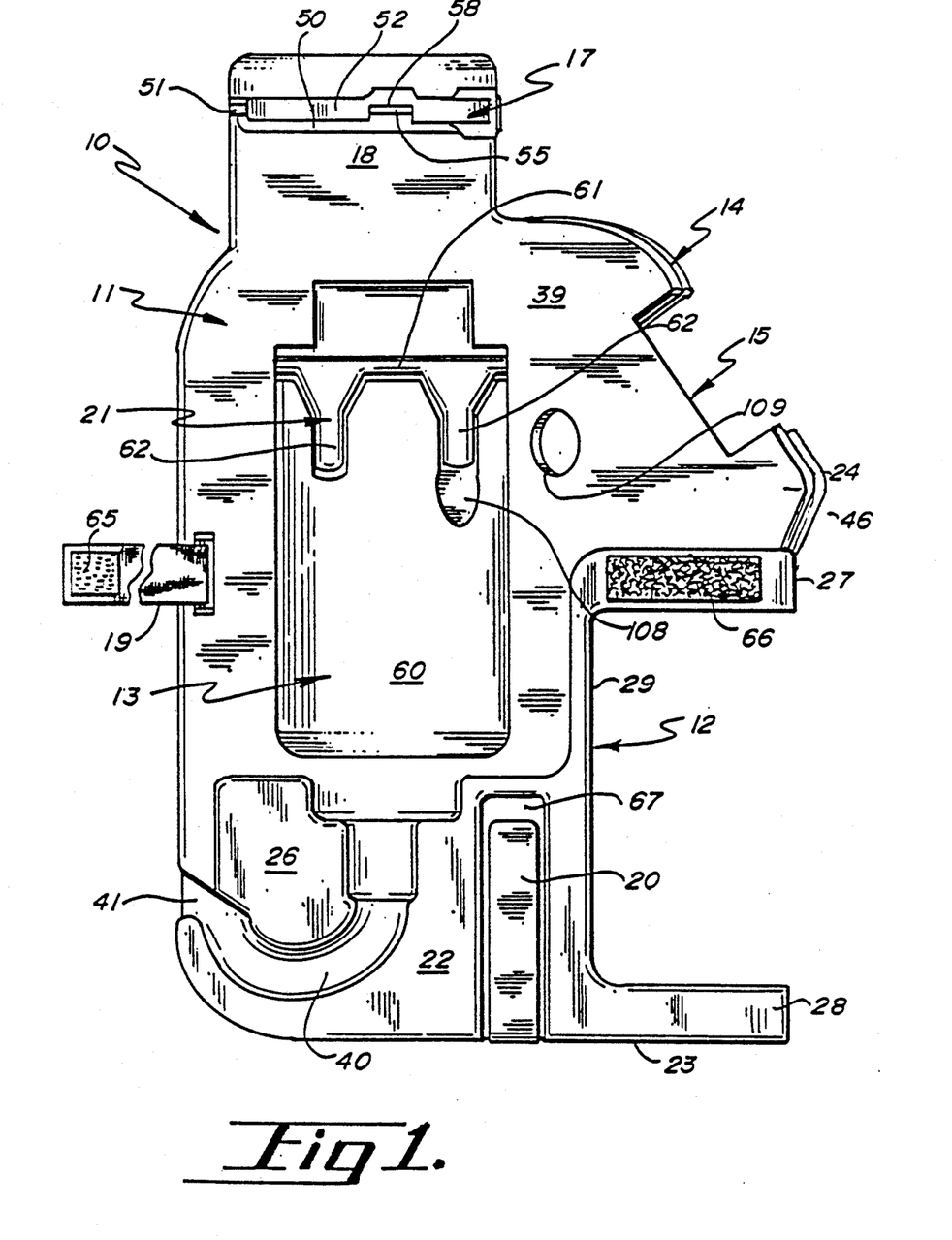
FIG. 1 is a front view of a support device made in accordance with the principles of the present invention.
Figures 4, 5A:
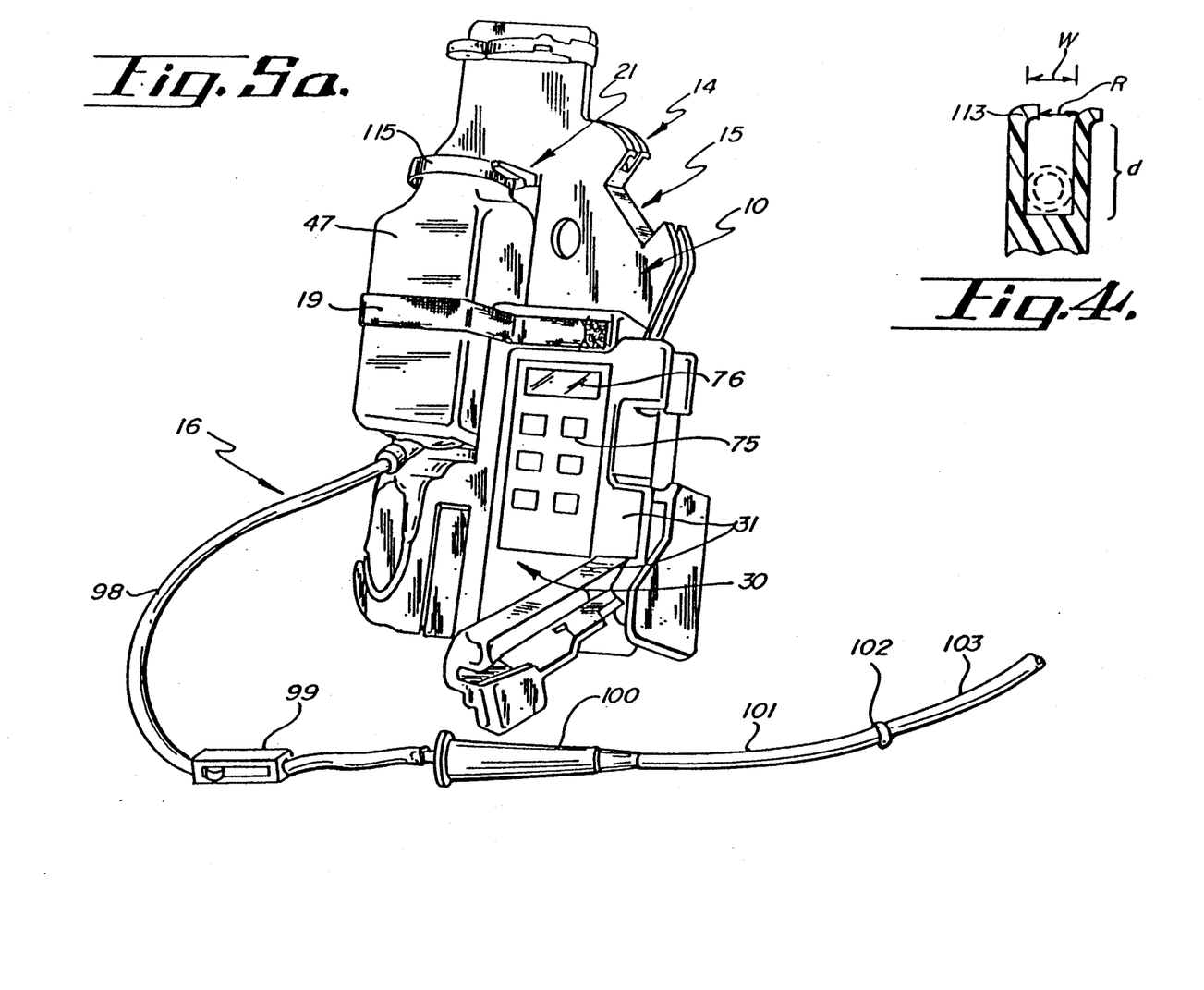

More specifically, as shown in FIG. 1, the support device 10 includes a generally rectangular rigid body 11 formed of rigid polymeric material or other lightweight material such as wood, metal alloy, etc. The body 11 is adapted to receive and retain a fluid delivery set and infusion pump of a fluid delivery system. Specifically, the body 11 forms a pump compartment 12 adapted to receive a standard infusion pump 30 (as shown in FIG. 5(a), a container compartment 13 adapted to partially receive a container from a standard fluid set 16 (as shown for example in FIG. 5(a), a tube channel 14 adapted to receive the tube of a standard fluid set, and a valve compartment 15 adapted to receive a pinch valve located on the tube of the fluid set.

The support device 10 also includes a plurality of fastening elements which are adapted for use in securing the fluid delivery system to the body 11 during use. These elements include a lid clamp 17 which is permanently affixed to a lid clamp extension 18 of the body 11, a securing strap 19 which is secured to the body 11, a saddle bracket 21 which is secured in a flush mount position in the bottom of container compartment 13, and a pump locking mechanism 25 (best shown in FIG. 2 and FIG. 8(b)) formed as a part of the base 23 of the body 11. The body 11 is also integrally formed with an elevated section 22 which, in cooperation with a similarly elevated section 26, forms part of the tube channel 14. Elevated section 22 also forms pump compartment 12.

Finally, if desired, an extendable leg 20 may be located in elevated section 22 so as to be flush therewith when the leg is in its retracted position, and to be extendable to a position perpendicular therewith and parallel to base 23 in its extended position. Leg 20 may also have an identical counterpart on the back surface 45 of the body 11 (as best seen in FIGS. 2 and 3).

The body 11 is preferably formed by a vacuum forming process well known in the prior art which includes vacuum forming a front surface 39 separate and apart from the back surface 45 and then permanently interconnecting the surfaces to complete the formation of the rigid body 11 in a well known manner. Alternatively, a reaction injection or other injection or other injection molding technology may be used.

Figure 2:
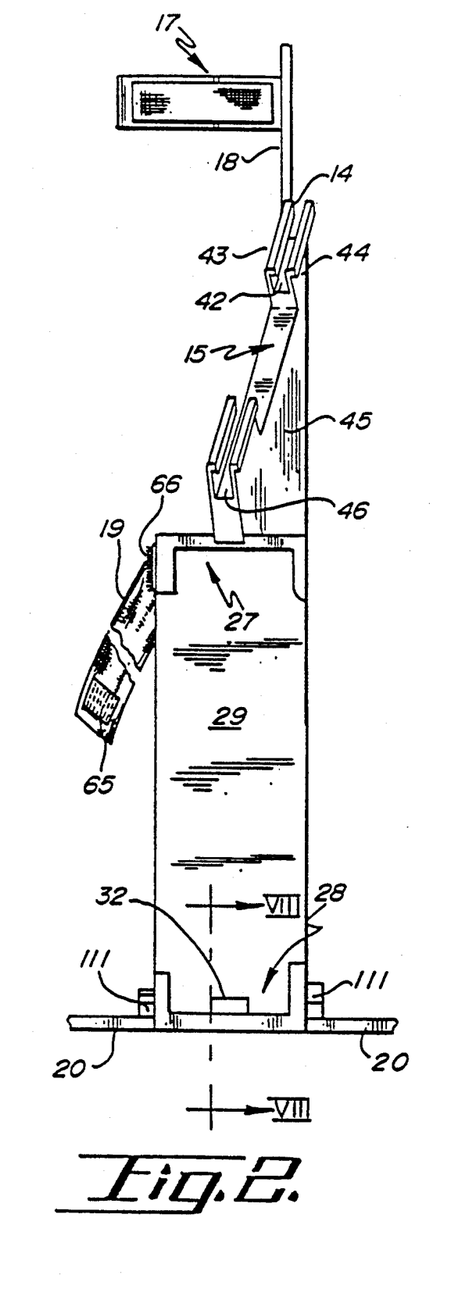
FIG. 2 is a side view of the support device of FIG. 1.
Figure 3:
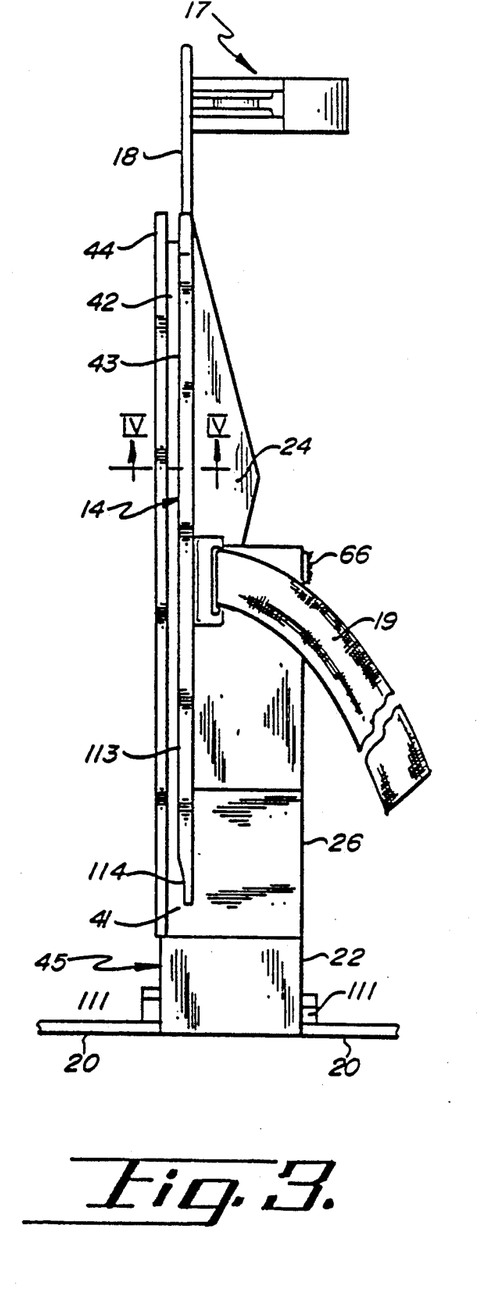
FIG. 3 is a side view of the support device of FIG. 1 opposite the side view of FIG. 2.

As best shown in FIGS. 1 and 2, the pump compartment 12 is formed of a generally C-shaped cavity having an upper and lower U-shaped channel 27 and 28, respectively, which are sized to receive a pump 30 in a sliding relationship (as shown in FIG. 5(a). U-shaped channels 27 and 28 are designed to allow the pump 30 to slide therein until it abuts with abutment surface 29.

The pump 30 is preferably a peristaltic-type roller pump which includes a hinged receiving arm 31 for receiving the tubing of a fluid set 16 (as shown in FIG. 5(a) in a manner as will be described momentarily.

Figure 8A:
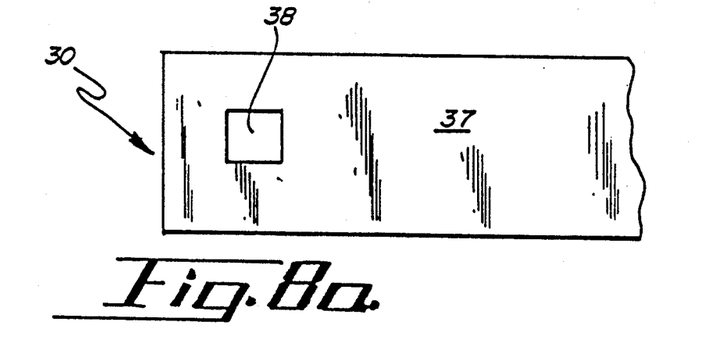
FIG. 8(a) is a bottom view of a transfusion pump.
Figure 8B:
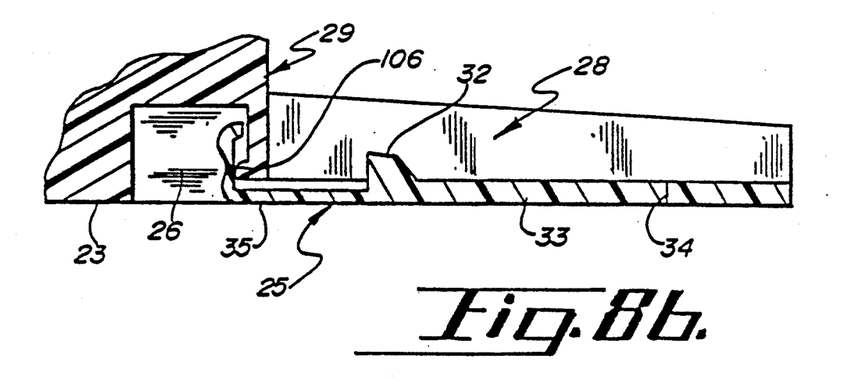
FIG. 8(b) is a cross-sectional view of a portion of the base of the support device showing the pump locking mechanism.

The lower U-shaped channel 28 is formed contiguously with the base 23 of the body 11 and includes the pump locking mechanism 25. As best shown in FIG. 2 and FIGS. 8A and B, the pump locking mechanism 25 includes an upwardly extending locking pin 32 integrally formed with a lever arm 33 which in turn is connected to base 23 at an end 34 thereof. It is intended that the arm 33 be somewhat flexible and may be a separate component affixed to the base 23 or may be integrally molded therewith. The opposite end 35 of the lever arm, adjacent lock pin 32, includes a release tab 35 which can be accessed through base opening 36 by a users finger in order to move the lock pin 32 into and out of locking position.

A stop member 106 is positioned to engage with release tube 35 when the lock pin 32 is moved out of locking position in order to prevent over extension of the locking mechanism 25. As best shown in FIG. 8A, the pump 30, on bottom surface 37 thereof includes a detent 38 which is sized and positioned so as to allow lock pin 32 to snap thereinto when pump 30 is properly positioned within the pump compartment 12. Positioning of the pump 30 within pump compartment 12 is accomplished by sliding the top and bottom of pump 30 into the upper and lower U-shaped channels 27 and 28, respectively. While the pump 30 is moving into the pump compartment 12, the bottom surface 37 thereof initially pushes lock pin 32 in a downward direction until the detent 38 becomes positioned thereover, after which the locking pin 32 snaps into position into the detent 38. The locking pin 32 then holds the pump within the pump compartment 12 until such time as the user pulls release tab 35 downwardly to withdraw lock pin 32 from the detent 38 and slides the pump 30 out of the pump compartment 12.

As shown in FIG. 1, the container compartment 13 is located generally centrally within the front surface 39 of the body 11. Container compartment 13 forms a generally rectangular recess within body 11 and is specifically sized to receive at least a portion of a fluid container of a fluid delivery set 16 in a manner as will be described momentarily.

Located below container compartment 13 are the elevated sections 22 and 26 of the body 11 which are oriented to form a tube path 40 for passing a tube from a container placed in container compartment 13 to the entrance 41 of the tube channel 14.

As best shown in FIGS. 2-4, the tube channel 14 of the support device 10 extends around approximately two thirds of the circumference of the body 11. The tube channel 14 is generally U-shaped in cross-section and includes a base 42, a front wall 43, and a back wall 44.

The tube channel 14 is essentially a channel between the front and back surfaces 39 and 45, respectively. The channel 14 extends from entrance opening 41 across the top and partially down the opposite side of body 11 to exit opening 46. Slightly above exit opening 46 the channel 14 is interrupted by a pinch clamp compartment 15 which is sized to receive a standard type pinch clamp commonly attached to the tubing of a fluid delivery set 16. The pinch clamp compartment 15 is formed by a cut out section of body 11 which is sufficiently large to allow a pinch clamp 99 (see FIG. 5(a)) to rest therein when the tubing to which it is attached is located in the tube channel 14 in a manner as will be demonstrated below.

As can be seen in FIG. 4, the channel 14 is designed to allow accommodation of the tubing of the fluid set 16 even though slight variations in length thereof may occur. This is because the channel 14 is of sufficient depth (d) to allow some "snaking" of the tube within the channel 14 if necessary to accommodate its entire length.

Further, the channel 14 is also designed to retain the tubing therein once place, even though some "snaking" may occur. Specifically, the channel is generally of a width (w) which is slightly larger than the diameter of the tube. However, at the top of the channel 14, the width (R) is restricted to a dimension less than the diameter of the tube.

The restriction is in the form of a lip 113 which ensures that the tubing stays with the channel. Without the pressure of the lip 113, the tube would have the mechanical inclination to bow outwardly and at least partially escape the channel at various locations around the body 11.

Because of the presence of the lip 113, it is advantageous to form a tapper 114 at the inlet opening 41 of the channel 14 for ease of beginning the insertion of the tube into the channel 14.

Due to the restricted width (R) of the channel 14 caused by the lip 113, the tube becomes resiliently deformed into an oval cross-sectional shape while passing into the channel 14. Once the tube is entirely in place within the channel 14, it will return to its circular cross-sectional shape and the tube will thereafter be retained within the channel 14 until forcibly withdrawn therefrom.

As best illustrated in FIG. 2, the forward sloping section 24 of the body 11 causes the exit opening 46 of the tube channel 14 to be positioned somewhat centrally over the pump compartment 12. This is advantageous in that it allows the tubing of the fluid delivery set to exit channel 14 at exit opening 46 in the proper position for reception into the hinged pump arm 31 of the pump 30 in the manner as also will be demonstrated below.

The support device 10 of the present invention is adapted to be able to receive and secure several different types of containers commonly used with standard fluid delivery sets 16. For example, as best shown in FIG. 1 and FIG. 5(d), container compartment 13 is recessed below front surface 39 of body 11, and shaped to receive a portion of a rigid blow molded type plastic bottle 47.

Figure 6A:
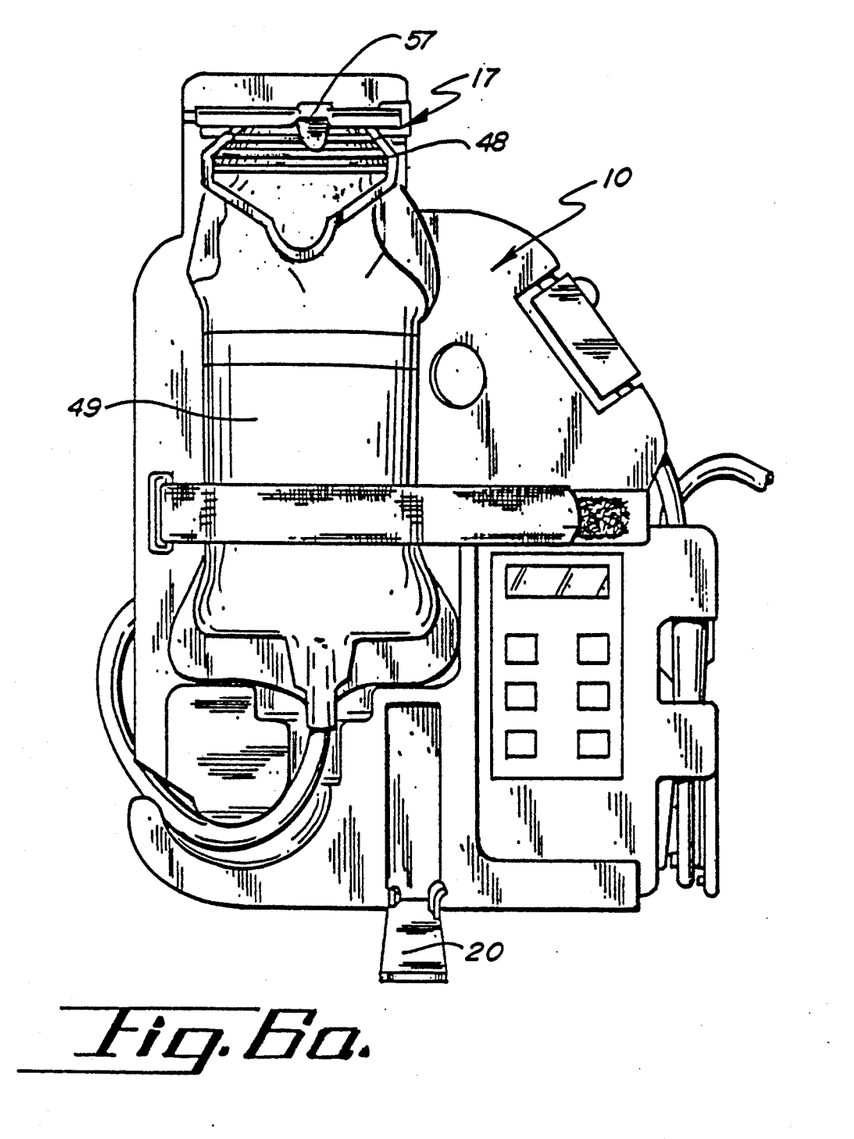
FIG. 6(a) is a front view of a support device made in accordance with the principles of the present invention including a soft bag-type container of a fluid delivery set.

Alternatively, as best shown in FIGS. 1 and 6(a), the body 11 can include a lid clamp extension 18 on its front surface 39, which extends above the container compartment 13 and which includes a lid clamp 17 oriented to receive the lid 48 of a soft flexible bag 49. The lid clamp 17 operates to secure the lid 48 of bag 49 in its proper position to allow the bag 49 to be properly located within container compartment 13. Also, and more importantly, the lid clamp 17 operates to prevent inadvertent bursting open of the lid 48 during use, such as may occur due to an exterior pressure being inadvertently applied to the bag 49.

Figure 7A:
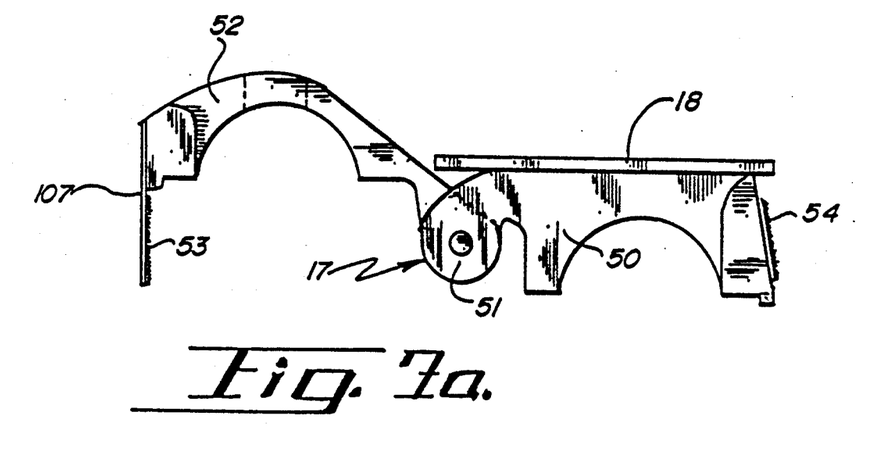
FIG. 7(a) is a top view of a lid clamp made in accordance with the principles of the present invention.
Figure 7B:
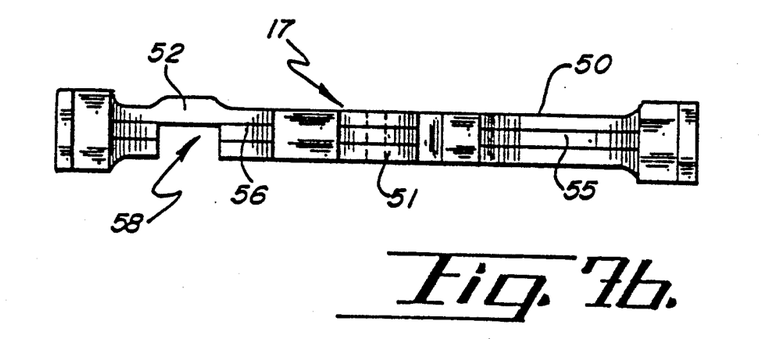
FIG. 7(b) is a front view of a lid clamp of FIG. 7(a)

As best shown in FIGS. 7(a) and 7(b), the lid clamp 17 includes a inner clamp jaw 50 permanently attached to the lid clamp extension 18. The inner jaw 50 is permanently attached through hinge 51 to an outer clamp jaw 52. A fastener such as a strap 107 including the pile portion 53 of a hook and pile type fastener may be attached to jaw 52, with the hook portion 54 of the fastener attached to jaw 50. The strap 107 allows the clamp 17 to be securely fixed in a closed position.

When in the closed position, the jaws 50 and 52 of the clamp 17 form a circular opening for receiving the mouth and lid 48 of the bag 49. The circular opening of the inner clamp jaw 50 forms an inner lip channel 55, and similarly, the outer clamp jaw 52 forms an outer lip channel 56 which will receive the circumferential edges of mouth and lid 48 of the bag 49. Also, since the lid 48 generally includes an opening tab 57 thereon, the outer clamp jaw 52 is formed with a tab opening 58 through which the tab 57 can extend when the clamp 17 is closed about the lid 48.

The lid clamp 17 can be positioned above container compartment 13 a sufficient distance to allow the accommodation of the desired size of bag 49. For example, the lid clamp extension 18 can be of a sufficient length to allow sufficient room in container compartment 13 to accept a bag 49 of the standard 1000 ml. volume. Alternatively, the lid clamp extension 18 may be somewhat shorter to allow the container compartment 13 to accept and properly position a bag 49 of standard 600 ml. volume.

Figure 6B:
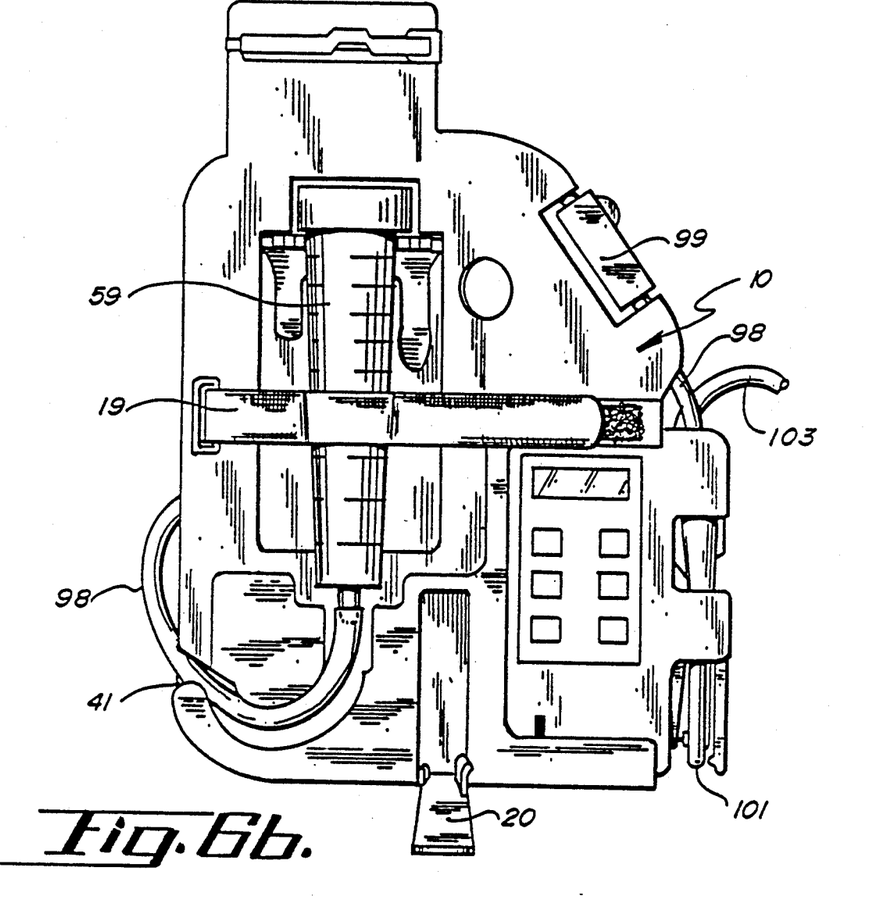
FIG. 6(b) is a front view of a support device made in accordance with the principles of the present invention including a burette-type fluid container of a fluid delivery set attached thereto.

Alternatively, as shown in FIG. 1 and FIG. 6(b), a burette-type container 59, commonly used with standard fluid delivery sets 16, can be partially fitted within container compartment 13 and held in place with the aid of strap 19 and saddle bracket 21.

Figures 9A, 11A:
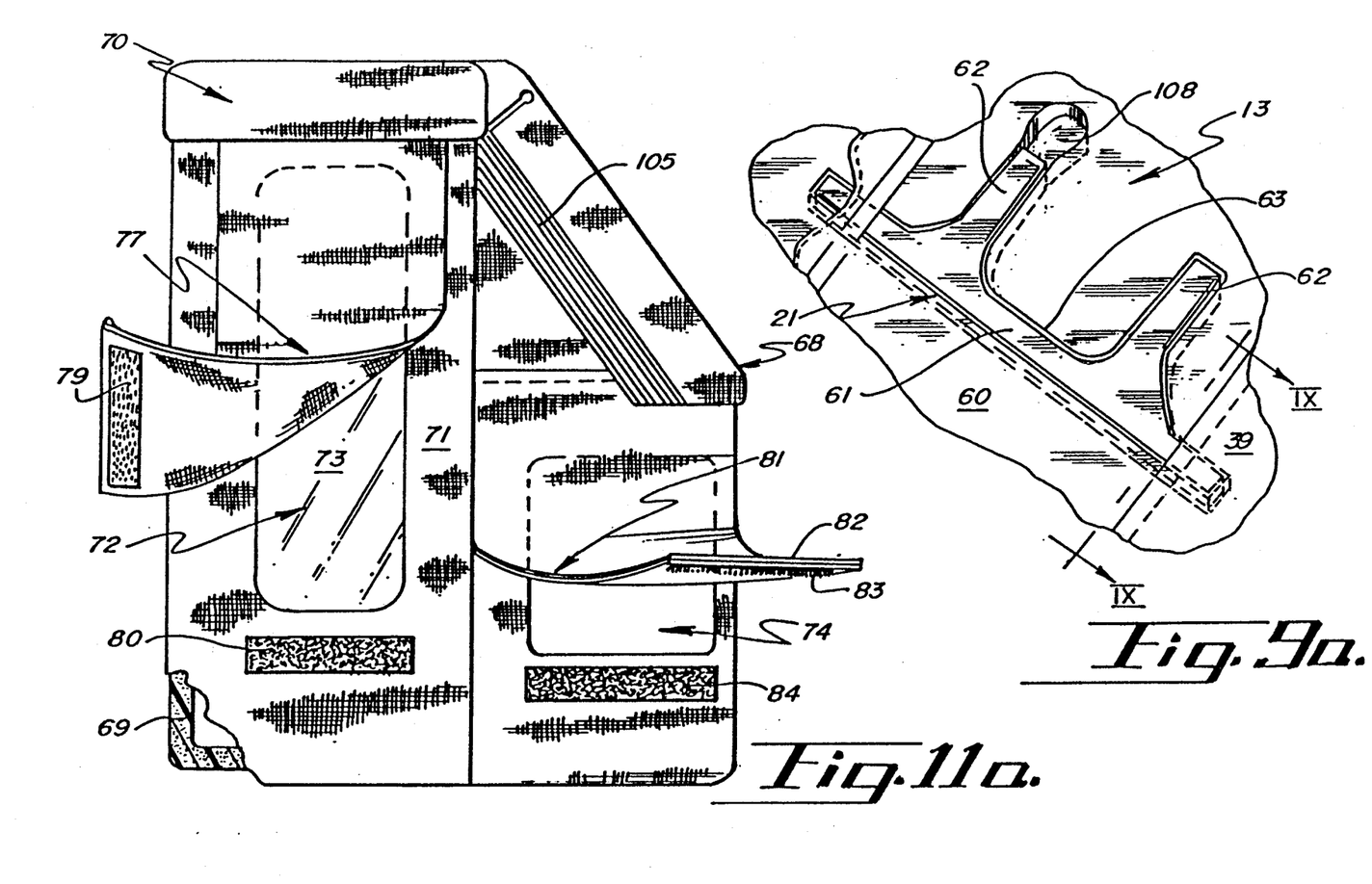
FIG. 9(a) is a partially cut away perspective view of a portion of the support device of the present invention showing the operation of the saddle bracket thereof.
FIG. 11(a) is a front view of a case for protecting the fluid delivery system of the present invention.

As best shown in FIGS. 1 and 9(a), the saddle bracket 21 is located within compartment 13 and flush mounted with the bottom 60 thereof. The bracket 21 includes a cross bar 61 and a pair of bracket arms 62 which extend perpendicularly therefrom and which are spaced apart from each other a distance slightly greater than the diameter of the burette 59. The bracket 21 can remain flush mounted within bottom 60 of the container compartment when not in use, and can be rotated 90 degrees to cause the bracket arm 62 to extend perpendicularly from bottom 60 of the container compartment 13 when used with the burette 59. The saddle bracket 21 can be used in a similar manner to support the mouth and lid 115 of the rigid plastic bottle 47 when used with the device 10 as will be explained below.

As can be best seen in FIG. 9(a), saddle bracket 21 rests within a cavity 63 in the bottom 60 of the container compartment 13. The cross bar 61 extends beyond the bracket arms 62 to pass into bracket arm mounting holes 64.

In use, the saddle bracket 21 can be lifted into its upright position by pulling bracket arm 62 upwardly from the cavity 63. This is most easily accomplished by inserting a finger into the cavity extension 108 and leveraging the arm 62 slightly out of the cavity 63. Bracket arm 62 can then be gripped from the container compartment 13 and rotated until they are in a perpendicular position relative to bottom 60.

Figure 9B:
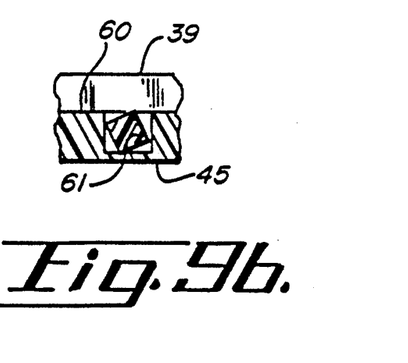
FIG. 9(b) is a cross-sectional view of the saddle bracket of the present invention taken along line IX—IX of FIG. 9(a)

As best shown in FIG. 9(b), the cross bar 61 and the bracket arm mounting hole 64 may be formed into square cross-sectional shapes with a large tolerance between the size of the mounting holes 64 and the cross bar 61 to allow a slight resilient deformation of the mounting hole 64 as the cross bar is rotated therein. Such a design causes the arms 62 of the bracket 21 to be biased into a flush position with bottom 60 of the container compartment 13 until they are rotated a full ninety degrees at which point the cross bar 61 is again properly oriented within mounting hole 64. Such a mounting design is commonly referred to as a "snap up" and/or "snap down" type mounting.

If desired, for additional support of a container placed in container compartment 13, a strap 19 is located on the front surface 39 of the body 11 in a position adjacent the container compartment 13 and is of sufficient length to cross over a container placed in container compartment 13 and be attached to the upper U-shaped channel 27 of the pump compartment 12 in a convenient manner such as by hook and pile fastener 65 and 66, respectively.

The support device 10 is adapted to be used with a pump 30 and fluid delivery set 16 in a variety of environments. For example, body 11 of the support device 10 includes a mounting hole 109 to allow the device 10 to be attached to a standard infusion pole for use with bed ridden or ambulatory patients. Alternatively, the device 10 may be placed on its base 23 on a level surface such as a table or the like without the need for any other mounting aid. In such an instance of use, the elevated section 22 of the front surface 39, and a generally opposing area of the back surface 45 may include support legs 20 flush mounted in recesses 67. The legs 20 can be rotated to an open position parallel with the surface 39 and flush with base 23.

Figure 10:
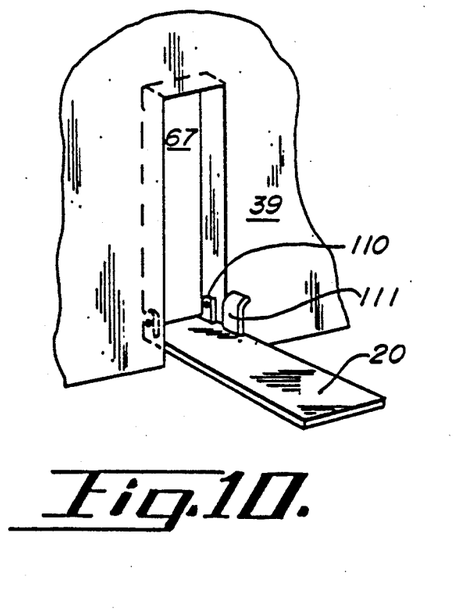
FIG. 10 is a perspective view of a leg of the support device in its extended position.

As best seen in FIG. 10, the leg 20 extends away from the front surface 39 of the body 11 to substantially increase the stability of the support device 10 when placed on a level surface. Similarly, another leg 20 can extend away from the back surface 45 in an identical manner. Each leg 20 rotates between its extended and retracted positions by means of hinges 110. Also, adjacent at least one hinge 110 on each leg 20 is a locking mechanism 111 which will flex into interfering position with the front surface 39 (or back surface 45) when the leg 20 is fully extended and will prevent inadvertent retraction of the leg 20. When it is desired to retract the leg 20 back into the recess 67, the locking mechanism 111 can be pushed laterally by the user to cause it to resiliently bend away interference with the surface 39 (or 45) and the leg 20 is simultaneously rotated into the recess 67 to its retracted position flush with surface 39 (or 45).

As a third alternative environment for use of the device 10 of the present invention, as best shown in FIGS. 11(a-d), a case 68 may be utilized to store the device 10, along with the pump 30 and fluid delivery set 16 attached thereto, in order to allow complete and convenient ambulatory use thereof.

The case 68 is formed generally to conform to the exterior shape of the support device 10 and includes semi-rigid foam lined walls 69 and cover 70. The front 71 of the case 68 includes a visual access opening 72, covered with a clear plastic panel 73, which allows visual access to the container when mounted to the support device 10 for use.

Front 71 of the case 68 also includes a control panel opening 74 which allows visual and physical access to the control panel 75 and display 76 of the pump 30.

The opening 72 is covered by a flap 77 which is sized so as to cover the entire opening 72 in a protective manner. The flap 77 can include an opening tab 78 and a fastening means such as hook and pile fasteners 79 and 80, respectively.

Figure 11B:
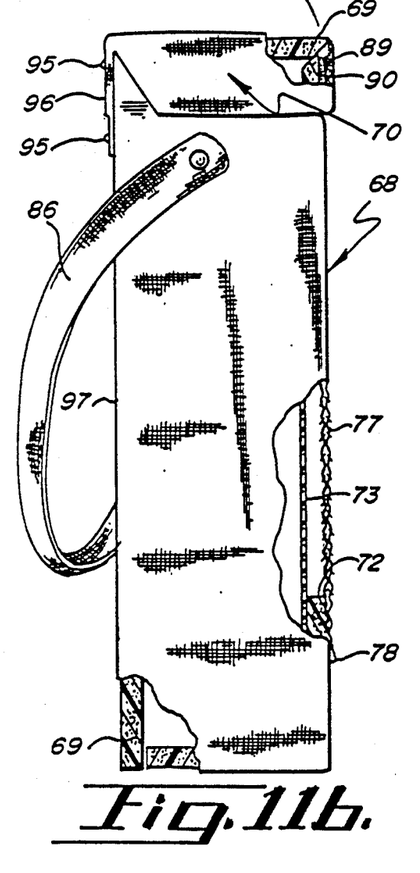
FIGS. 11(b) and 11(c) are side views of the case of FIG. 11(a)
Figure 11C:
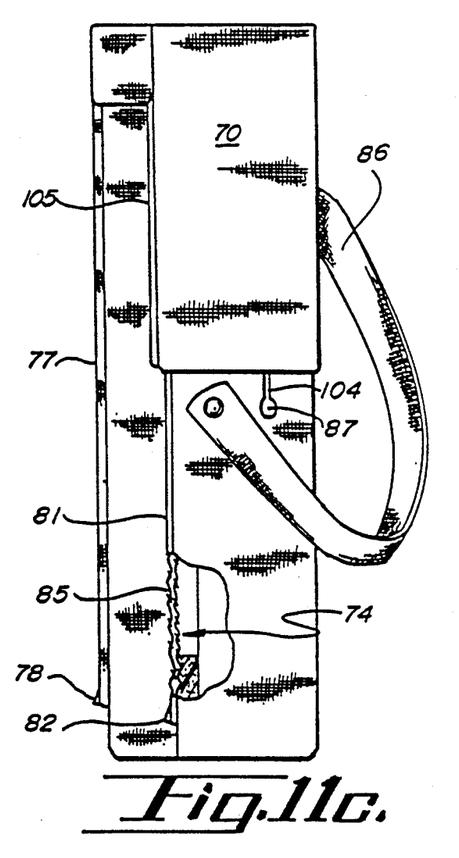
Figure 11D:
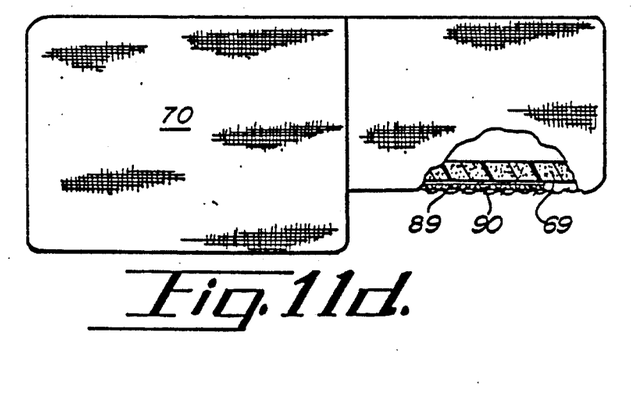
FIG. 11(d) is top view of the case of FIG. 11(a)

Control panel opening 74 also includes a flap 81 sized to completely cover the opening 74 to protect the pump 30. Flap 81 may also include an opening tab 82 and hook and pile type fasteners 83 and 84, respectively. Further, as best shown in FIG. 11(c), flap 81 may also include a semi-rigid protection panel 85 which will supply added protection against accidental control panel activation or damage to the pump 30 due to an inadvertent blow to the case 68. As best shown in FIGS. 11(b and c), the case 68 can include a carrying strap 86 for allowing the case to be carried on the shoulder, back or around the waist of the patient while ambulatory.

As best shown in FIG. 11(c), the case also includes a tube outlet 87 to allow tubing 103 (see FIG. 5(a)) exiting the pump to pass outside of the case 68 to be attached to the patient.

Figure 12:
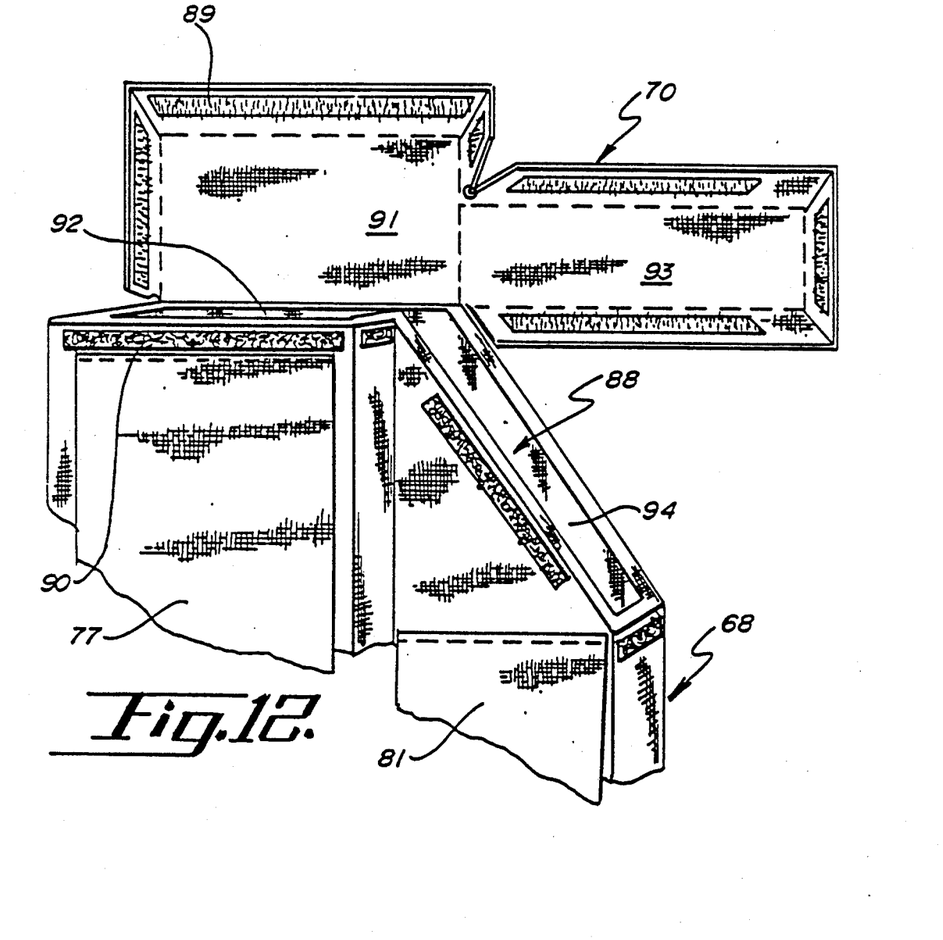
FIG. 12 is perspective view of the case showing a preferred embodiment of the cover thereof in its open position.

As best shown in FIG. 12, the cover 70 of the case 68 can be formed to accommodate the irregularly shaped case opening 88. The cover 70 may include hooks 89 around the entire inner circumference thereof which can fasten to piles 90 located around the outer perimeter of the top of the case 68. The cover 70 may also include a first portion 91 sized to cover a first portion 92 of the case opening 88 while a second portion 93 of the cover may be adapted to conform to a second portion 94 of the case opening 88 which is oriented at an angle relative to the first portion 92. As best seen in FIG. 11(b), the entire cover 70 may be attached to the case 68 such as by the stitching 95 to secure a single flap 96 of the cover 70 to the back surface 97 of the case 68. Similarly, the flaps 77 and 81 may be stitched or otherwise permanently attached at the upper most portions thereof, and carrying strap 86 may be riveted or otherwise permanently secured to the case 68.

Figure 13:
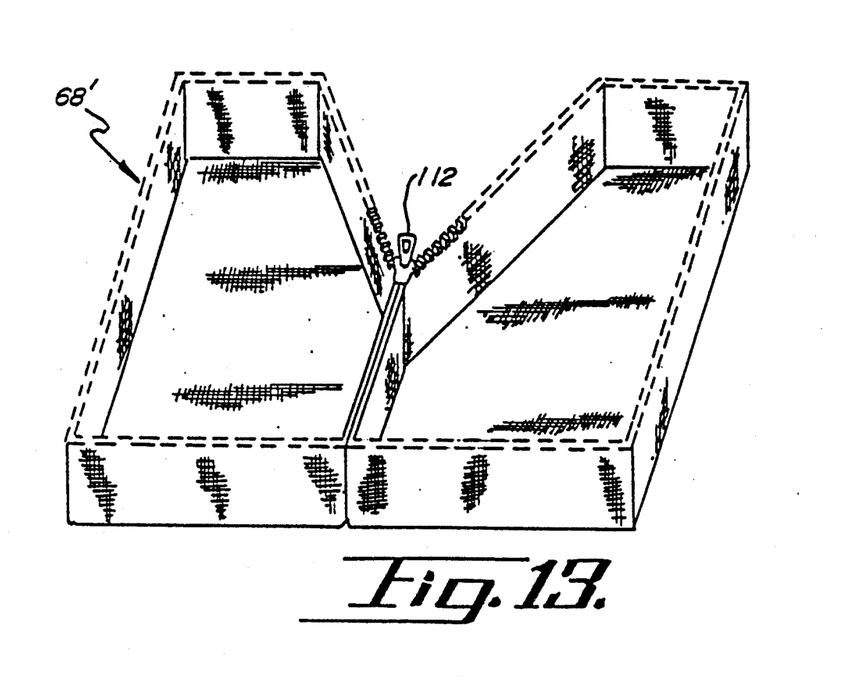
FIG. 13 is a perspective view of the case of the present invention as described in FIGS. 11(c-d), with an alternative opening and closing design.

An alternative embodiment of the case 68 is shown in FIG. 13. The case 68' is substantially similar to case 68 except that there is no cover 70. Alternatively, the case 68' is formed substantially in two halves which are fixed together at a single common side thereof. The case 68' thus opens and closes in a "clam-shell" fashion. The case 68' may be secured in its closed position in any well known manner, preferably by a zipper 112 which extends around the majority of the circumference of the case 68'.

As best shown in FIG. 5(a), the fluid delivery set 16 includes a container such as the plastic bottle 47, with a standard length of tubing 98 extending therefrom which is in fluid communication with the bottom thereof. The tubing 98 includes a pinch valve 99 thereon and a drip chamber 100 attached at the end thereof. The opposite end of the drip chamber 100 is attached to an extensible relatively thin-walled pump roller tube 101 which especially adapted for use with the pump 30. An extension ring 102 is attached to pump tubing 101 and functions to insure that the pump tubing 101 is properly stretched over the rollers (not shown) of the pump 30. Beyond extension ring 102 is an infusion tube 103 which is intended to be attached to the patient. It is to be understood that although the present invention is being described for use in conjunction with specific fluid delivery sets 16 and a specific pump 30, any well known type fluid delivery sets or infusion pump may be used with or adapted for use with the support 10 of the present invention and remain within the intended scope and meaning of the present disclosure.

Referring now to FIGS. 5(a–d), the method attachment of a fluid delivery set 16 including the rigid bottle 47, and a pump 30 to the support device 10 of the present invention is described as follows. In FIG. 5(a), the pump 30 is inserted into pump compartment 12 until it is locked in position by pump locking mechanism 25. The saddle bracket 21 is lifted to its "pop-up" position and the bottle 47 is inserted into the container compartment 13 until tubing 98 thereof can extend into the tube path 40. In this position, the bracket 21 secures the mouth and lid 115 of the bottle 37 against lateral movement. The strap is then secured over bottle 37 to prevent its escape from the compartment 13. The tube 98 is then grasped and forced into entrance 41 of tube channel 14 and drawn the entire length of channel 14 until pinch valve 99 is reached.

Figure 5B:
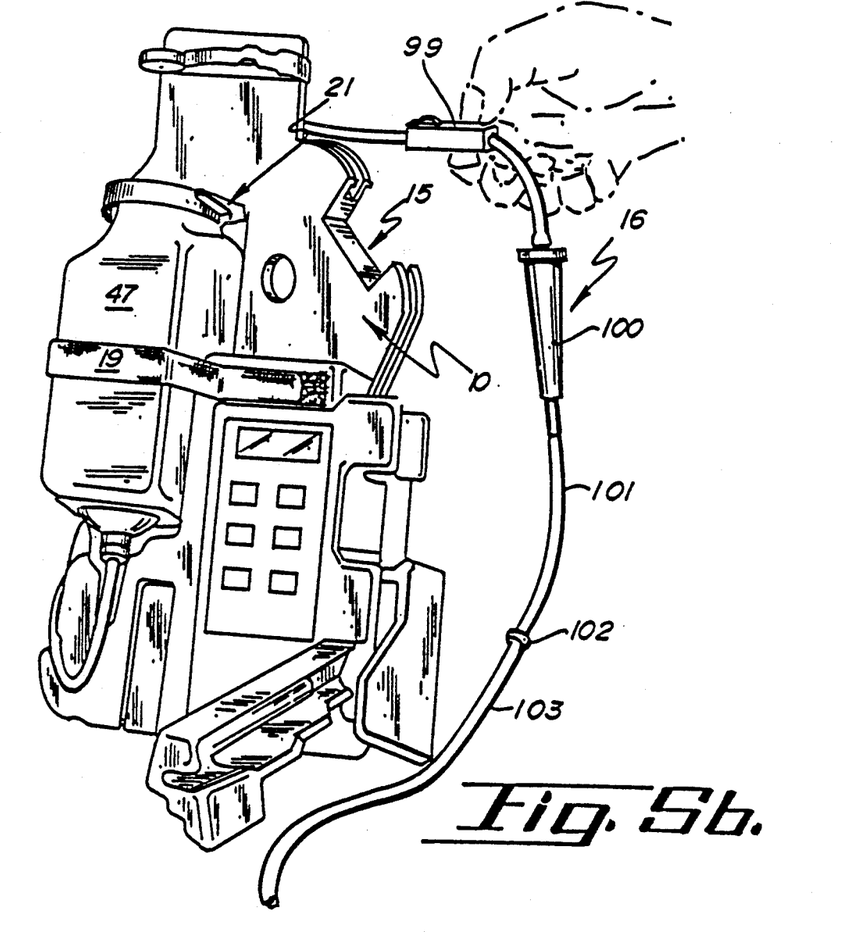

As shown in FIG. 5(b), pinch valve 99 is adjusted along tubing 98 until it is oriented properly to be received in pinch valve compartment 15. Tubing 98 is then extended through the remainder of tubing channel 14 and allowed to extend beyond exit 46.

Figure 5C:
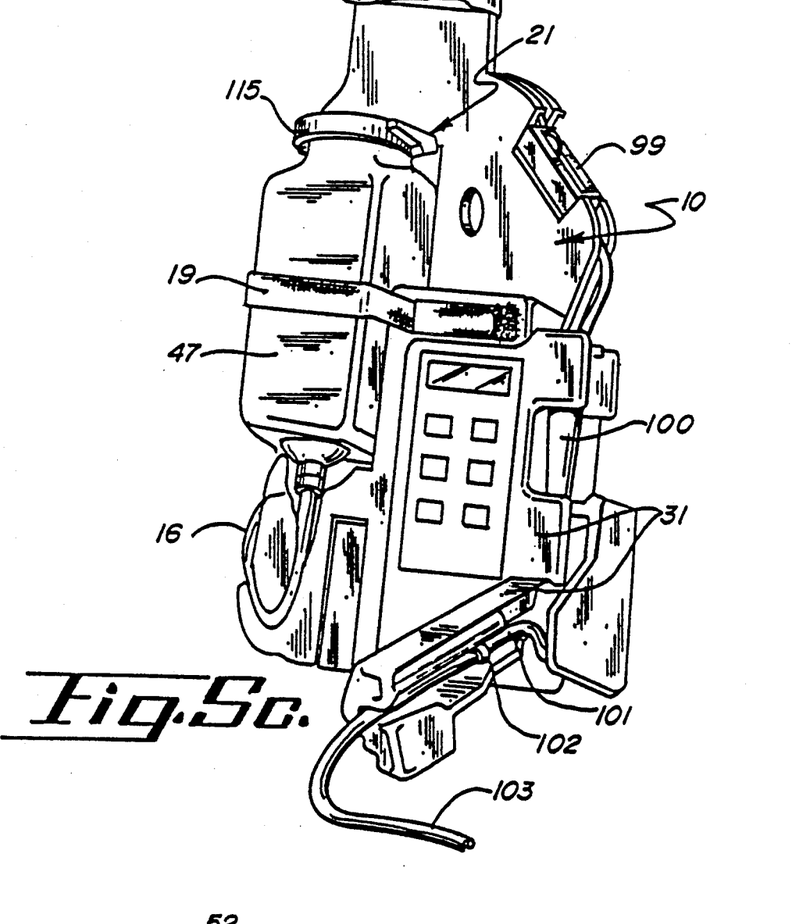
Figure 5D:
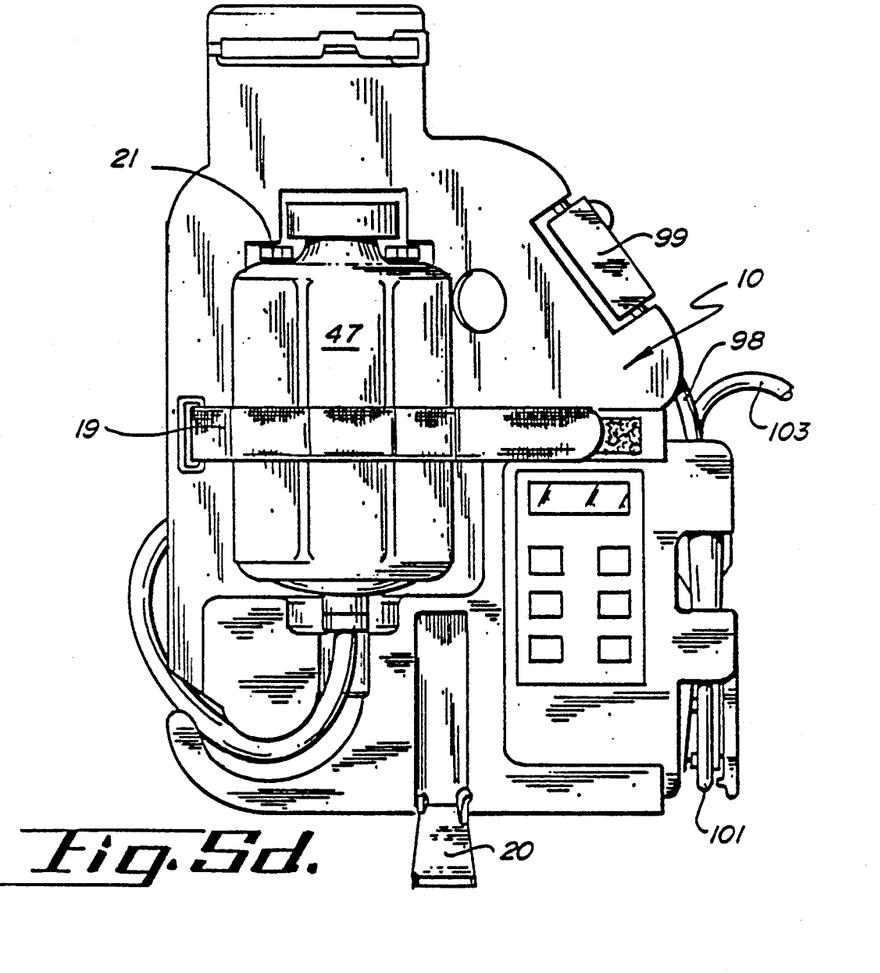

As best shown in FIG. 5(c), the drip chamber 100 is inserted into the hinged arm 31 of the pump 30 and pump tubing 101 is passed around the pump rotors until the retention ring 102 is properly positioned in a slot within the arm 31 in such a manner as will cause the tube 101 to be stretched over the rollers of the pump 30 when the arm 31 is moved to its closed position.

As shown in FIG. 5(d), the pump arm 31 is then rotated into its closed and operating position and the infusion tube 103 extends away from the pump arm toward the patient.

If desired, the support device may be placed on an infusion pole by inserting a hook thereof (not shown) through hole 109. Alternatively, legs 20 may be extended and the support device 10 may be rested on its base 23 on a horizontal surface such as a table or the like. Finally, should the patient wish to be completely ambulatory, the support device may be inserted into the case 68 or 68' with the infusion tube 103 extending out of the case by passing it through the tubing outlet opening 87.

As best shown in FIG. 6(a), a fluid delivery set including a flexible bag 49 is attached to the support device 10 in an manner similar to that described in FIGS. 5(a–d) with respect to the rigid bottle type fluid infusion set 16, except that the lid 48 of the flexible bag 49 is inserted into the lid clamp 17 and securely clamped in place.

Similarly, as shown in FIG. 6(b), a fluid infusion set 16 including a burette type container can be positioned in the support device 10 in a manner similar to that described with respect to the rigid bottle in FIGS. 5(a–d), except that the saddle bracket 21 is first rotated to its "snap up" position and the burette 59 is placed between the bracket arms 62.

With each type of fluid infusion set, if desired or necessary, the strap 19 may be used to secure the container and the container compartment 13. Although not shown, other standard fluid sets 16, such as spike sets, etc. can be similarly used with the support device 10 of the present invention.

It will be apparent from the foregoing, while particular embodiments of the invention have been illustrated and described, various modifications can be made thereto without departing from the spirit and scope of the present invention. Accordingly, it is not intended that the invention be limited, except as by the appended claims.

What is claimed is:

1. A support device for a fluid delivery system including a fluid delivery set and a pump, the fluid delivery set including a fluid container and a tube for connection to the pump, said device comprising
a rigid body means having:
a first compartment means for holding the pump,
a second compartment means for holding the container in fixed position relative to said rigid body means, and
a third compartment means for preventing kinking or occlusion of the tube between the container and the pump, said third compartment means forming a channel extending around a substantial portion of a circumference of said rigid body means;
wherein said rigid body means maintains said first compartment means, said second compartment means and said means for preventing kinking or occlusion of the tube, in fixed spaced apart relationship relative to each other.

2. A support device according to claim 1 wherein said third compartment means is capable of substantially enclosing the majority of the length of the tube between the container and the pump.

3. A support device according to claim 2 wherein said rigid body means includes a fourth compartment means, whereby, a pinch clamp included on a tube of a fluid delivery set may be located within said fourth compartment means when the tube is properly located within said third compartment means.

4. A support device according to claim 1 wherein said channel is generally U-shaped.

5. A support device according to claim 4 wherein said means for resiliently deforming said tube is an elongated lip formed along at least a portion of said elongated opening of said channel.

6. A support device according to claim 1 wherein said channel forms an elongated opening through which the tube can be inserted, and said opening includes means for resiliently deforming the tube as it passes into said channel.

7. A support device according to claim 5 wherein said channel forms an inlet opening adjacent a first end of said elongated opening, and a exit opening adjacent a second end of said elongated opening, said inlet opening being located on said circumference of said rigid body means so as to conveniently receive the tube from the container when located in said second compartment means, and said exit opening being located on said circumference of said rigid body means adjacent said first compartment means so as to allow the tube to pass directly from said channel to the pump when located in said first compartment means.

8. A support device according to claim 1 wherein said first compartment means for holding the pump includes means for locking said pump within said first compartment means.

9. A support device according to claim 8 wherein said means for locking the pump in said first compartment means includes a locking pin attached to a resilient lever arm means,
whereby said locking pin can be moved from a first position in which it can lock the pump in place within said first compartment means and a second position wherein said pump can be removed from said first compartment means, said movement from said first to said second position being accomplishable by resilient displacement of said lever arm.

10. A support device according to claim 1 wherein said second compartment means for holding the container is formed as a recess within a front surface of said rigid body means, said recess including a substantially flat bottom surface against which a portion of the container rests when properly placed in said second compartment means.

11. A support device according to claim 1 include means attached to said rigid body means for securing the container in proper position within said second compartment means.

12. A support device according to claim 11 wherein said means for securing the container within said second compartment means includes strap means attached to said rigid body means and operable to partially surround a container located in said second compartment means to aid in securing said container in said compartment means.

13. A support device according to claim 11 wherein said means for securing the container in said second compartment means includes means for securing a substantial portion of a mouth and lid of the container in relatively fixed position relative to said rigid body means.

14. A support device according to claim 13 wherein said means for securing the mouth and lid of the container includes a clamp means attached to said rigid body means for substantially surrounding the mouth and lid of the container.

15. A support device according to claim 13 wherein said means for securing the mouth and lid of the container includes a U-shaped bracket means adapted to receive the mouth and lid of the container therein when the container is properly positioned in said second compartment means.

16. A support device according to claim 15 wherein said U-shaped bracket means is located within said second compartment means.

17. A support device according to claim 16 wherein said second means for holding the container is formed as a recess within a front surface of said rigid body means, said recess including a substantially flat bottom surface against which a portion of the container rests when properly placed in said second compartment means, and said U-shaped bracket means is mounted within said flat bottom surface and is operable between a first position in which said U-shaped bracket means is flush with said flat bottom surface, and a second position in which said U-shaped bracket means is rotated approximately 90 degrees to be substantially perpendicular to said flat bottom surface.

18. A support device according to claim 1 further including leg means attachable to rigid body means and rotatable between a first position in which said leg means are oriented flush with a front surface of rigid body means, and a second position in which said leg means is oriented flush with a base surface of rigid body means.

19. A support device according to claim 18 wherein said leg means includes locking means for maintaining said leg means in said second position.

20. A support device according to claim 1 further including case means for enclosing said rigid body means with said fluid delivery system attached thereto.

21. A support device according to claim 20 wherein said case means forms a first opening through which the container can be viewed when located within said case means, and a second opening through which said pump can be viewed when located within said case means.

22. A support device according to claim 21 wherein said case means further includes removable covering means for covering said first and second openings of said case means.

23. A support device according to claim 22 wherein said covering means for removably covering said second opening further includes a rigid stiffening member therein.

24. A support device according to claim 23 wherein said case means further includes a third opening through which said rigid body means can be inserted and a cover means for securely closing said third opening.

25. A support device according to claim 20 wherein said case means is formed substantially of two similar halves reversibly separable by a fastening member whereby, said case means may be opened in clam-shell fashion to allow insertion of said rigid body means and subsequently reclosed by said fastening member.

26. A support device according to claim 1 wherein said first compartment means is formed on an exterior surface of said rigid body means.

27. A support device for a fluid delivery system including a fluid delivery set and a pump, the fluid delivery set including a fluid container and a tube for connection to the pump, said device comprising
 a rigid body means having:
  a first compartment means for holding the pump,
  a second compartment means for holding the container, and
  a third compartment means for holding a tube between the container and the pump, said third compartment means extending around a substantial portion of a circumference of said rigid body means,
 whereby, excess tubing between the container and pump is held against kinking or occlusion by said third compartment means.

* * * * *